United States Patent [19]
Wang

[11] Patent Number: 4,890,626
[45] Date of Patent: Jan. 2, 1990

[54] REMOVABLE LOCKING DEVICE FOR USE WITH SYRINGES
[76] Inventor: Ko P. Wang, 11006 Nacirema La., Stevenson, Md. 21153
[21] Appl. No.: 222,096
[22] Filed: Jul. 18, 1988

Related U.S. Application Data
[62] Division of Ser. No. 897,936, Aug. 19, 1986, Pat. No. 4,791,937.
[51] Int. Cl.$^4$ ............................................. A61B 10/00
[52] U.S. Cl. .................................. 128/752; 128/763; 604/220; 604/223
[58] Field of Search ............... 128/751, 752, 753, 754, 128/760, 763; 604/187, 218, 220, 223

[56]  References Cited
U.S. PATENT DOCUMENTS 3,747,812  7/1973  Karman et al. ...................... 604/236
4,532,935  8/1985  Wang ................................. 128/753
4,610,672  9/1986  Ewalt et al. ........................ 604/220

Primary Examiner—Max Hindenburg
Assistant Examiner—Randy Shay
Attorney, Agent, or Firm—Cushman, Darby & Cushman

[57]  ABSTRACT

A biopsy needle assembly comprised of an outer flexible catheter and a reciprocating interior structure on which the needle is mounted. In one embodiment, the needle is directly connected to an internal guide wire. In another, the needle is directly connected to an inner flexible catheter and the guide wire can either extend through the needle or be stopped within the needle. In each embodiment, the needle includes a lateral opening providing a fluid path from the hollow needle, through the catheter, either between the catheter and guide wire or the inner and outer catheters to an outlet at the proximal end of the assembly. The invention also relates to a syringe plunger stop end lock attachment.

2 Claims, 6 Drawing Sheets

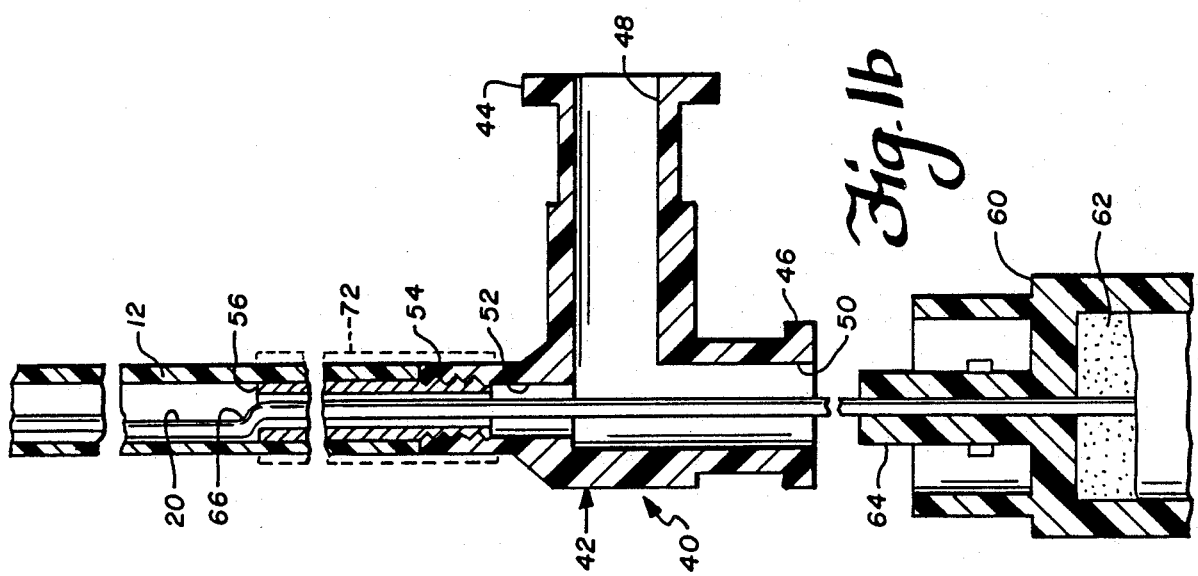

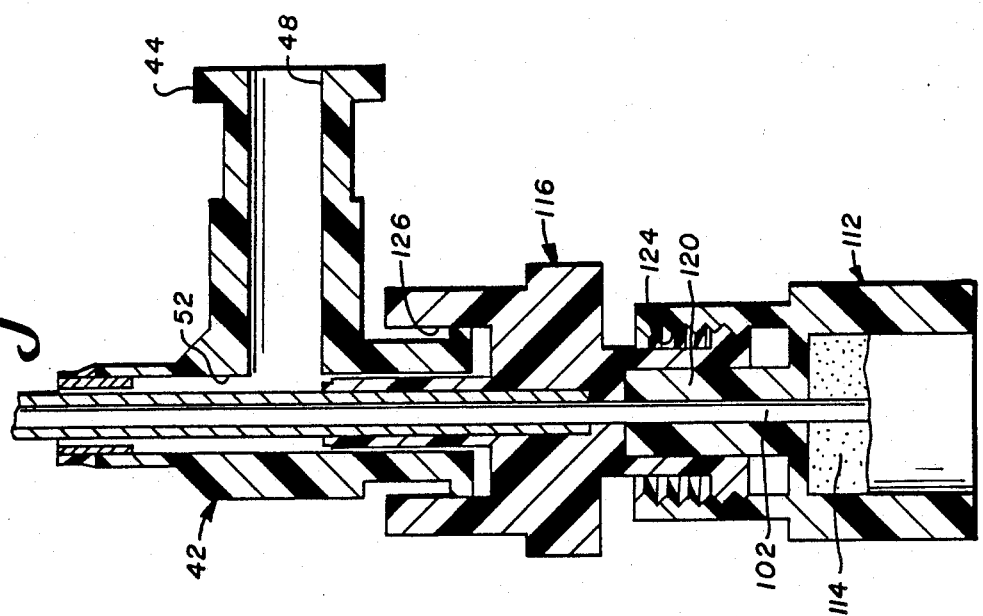
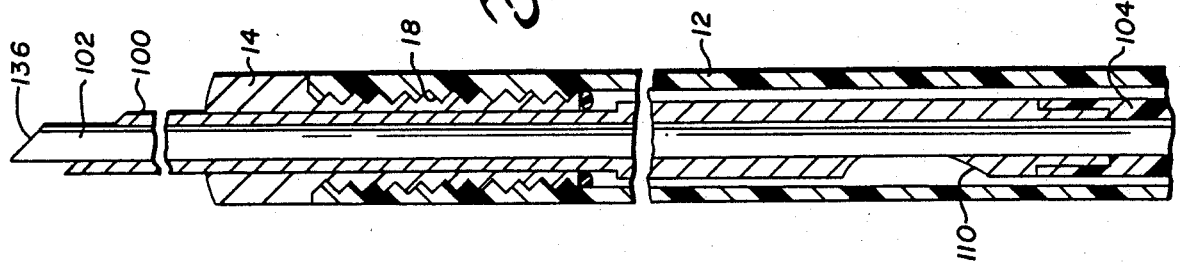
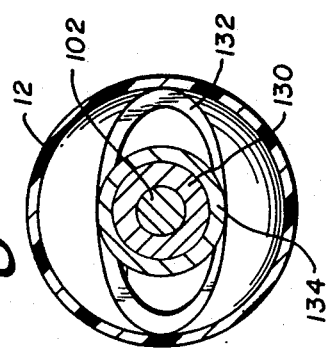
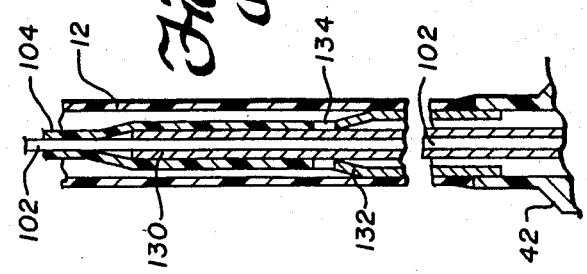

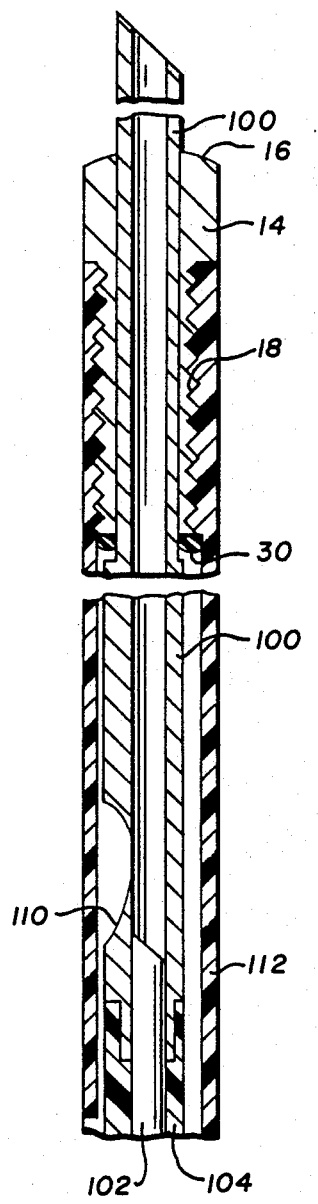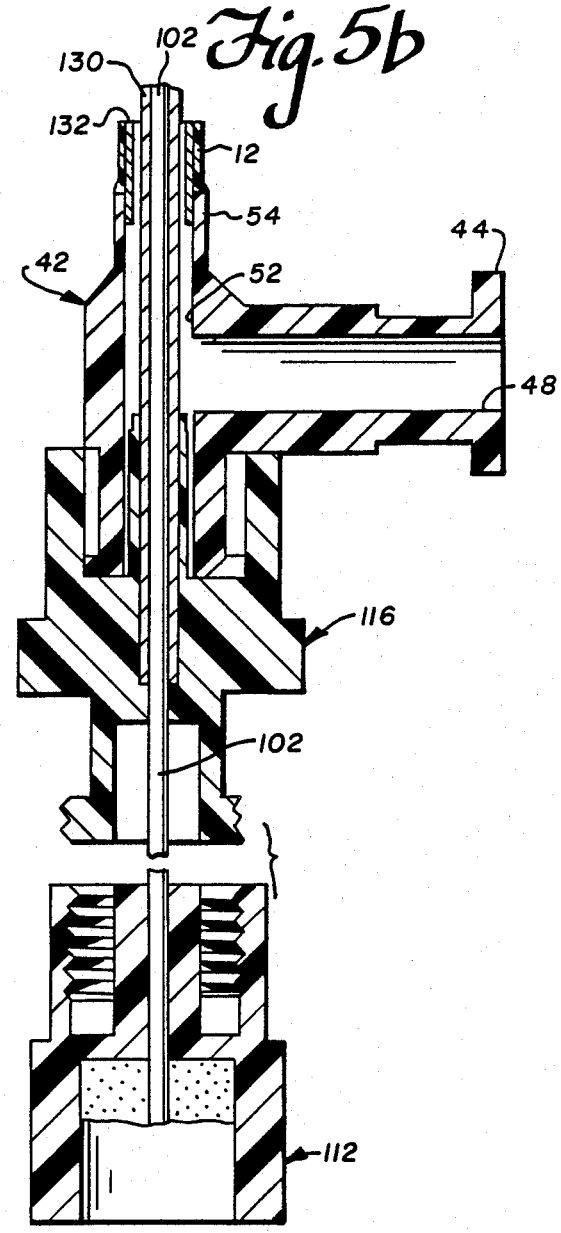

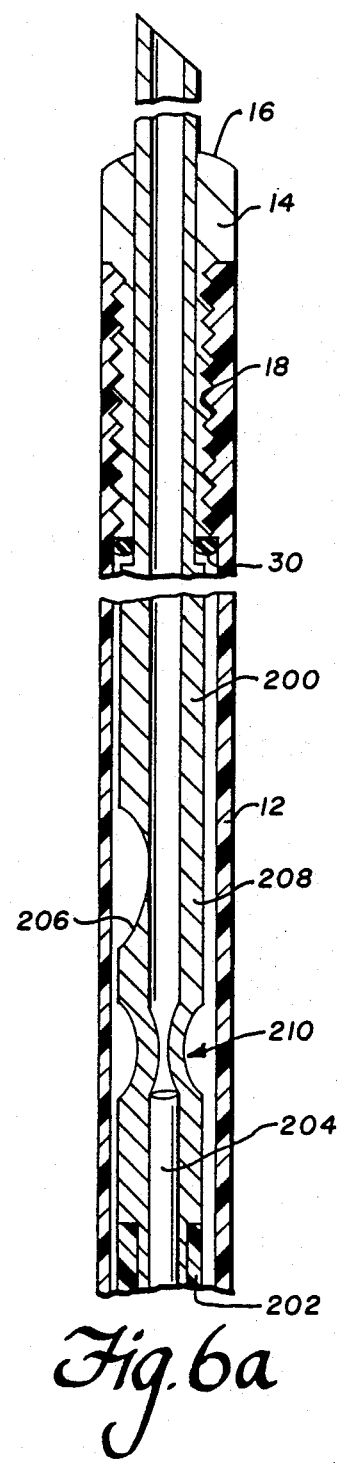
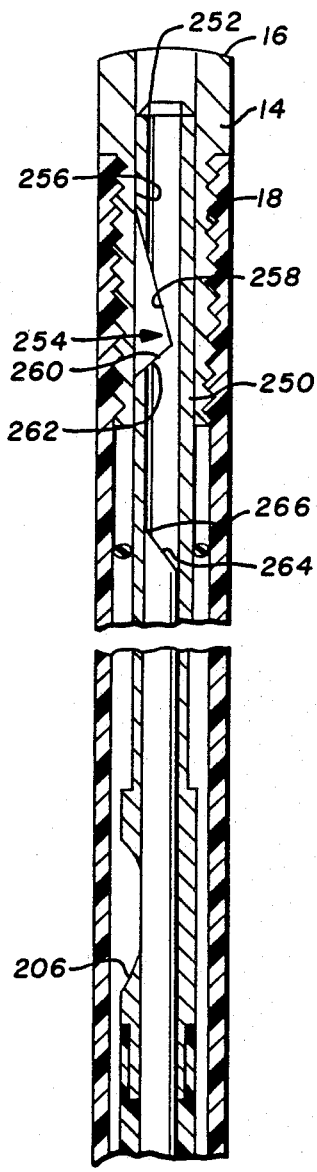
Fig. 6a
Fig. 6b

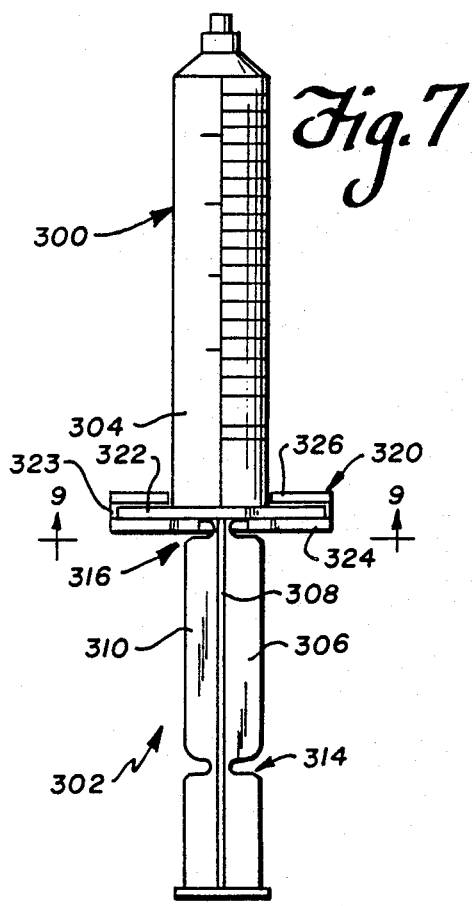
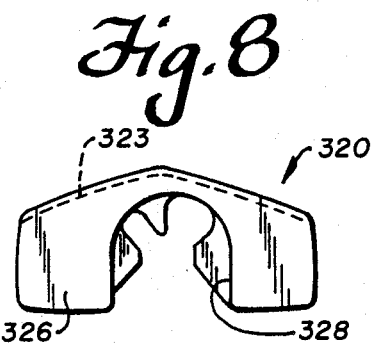
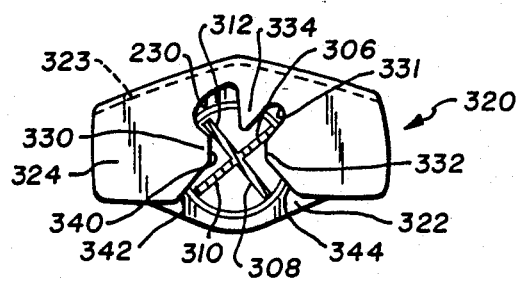
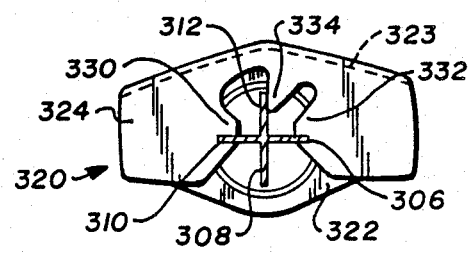
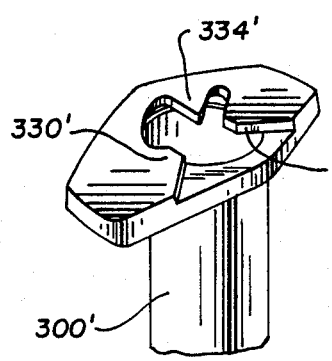

REMOVABLE LOCKING DEVICE FOR USE WITH SYRINGES

This is a divisional application of Ser. No. 897,936, filed Aug. 19, 1986, now U.S. Pat. No. 4,791,937.

FIELD OF THE INVENTION

The present invention relates to a transendoscopic biopsy needle, for use with a flexible bronchoscope, endoscope or any type of body cavity scope, for obtaining tissue specimens from within the body.

RELATED APPLICATIONS

This application relates to similar subject matter as in my earlier U.S. Pat. No. 4,532,935 entitled Bronchoscopic Needle Assembly, as well as my copending U.S. patent applications Ser. No. 709,648, entitled Bronchoscopic Needle Assembly, filed on Mar. 8, 1985, now U.S. Pat. No. 4,617,940, Ser. No. 438,245, entitled Bronchoscopic Needle Assembly, filed on Nov. 1, 1982, No. U.S. Pat. No. 4,766,906 Ser. No. 723,90 entitled Flexible Bronchoscope Needle, Assembly, filed on Apr. 16, 1985, now U.S. Pat. No. 4,702,260 and Ser. No. 260,602 entitled Bronchoscope Needle, filed on May 6, 1981 (now abandoned) the disclosures of each being expressly and fully incorporated hereinto by reference.

BACKGROUND OF THE PRESENT INVENTION

As is set forth in the above patents and patent applications, the inventions, including the present one deal with flexible biopsy needle assemblies that allow biopsy tissue samples to be obtained through substantially non-invasive procedures performed on patients by utilizing the flexible needles of these inventions together with an endoscope or bronchoscope. Following insertion of the endoscope or bronchoscope within a body cavity, the flexible biopsy needle assembly is slideably inserted into a passageway provided therefor within the scope. Once positioned adjacent the tumor or the area where tissue is to be sampled, the needle portion of the assembly will be exposed into the tissue. Insertion of the needle into the tumor can be repeated, by and inserted applying force on the proximal end of the apparatus so that through the compressive properties of the apparatus provided by the internal stylet the applied force will be transmitted to the needle. This technique, when used in the bronchial area, has come to be referred to as a transbronchial needle asperation biopsy procedure. Tissue samples can be obtained from directly within the bronchial passageways, the lungs or from tumors located on the body side of these areas. For example, by using this needle assembly one can obtain mediastinum tissue located outside of the bronchial airways. Prior to the development of this technique, such tissues could only be obtained by invasive surgical procedures which are not only more dangerous to a patient but cause various types of suffering and are costly.

In obtaining the tissue sample within the needle it is necessary to apply some negative pressure or suction to the needle once the needle is inserted into the tissue to help assure tissue collection. In my prior needle assemblies, a stylet or guide wire was used internally within the needle assembly to provide, sufficient rigidity to thread the needle and catheter assembly through the bronchoscope and during tissue penetration as well as to provide protection for the tip of the needle end to protect the interior lining of the bronchoscope channel. Also, by allowing the guide wire to extend beyond the needle protected the patient from inadvertent needle damage. However, to apply suction to the needle it was necessary to remove the guide wire thereby developing a sufficient suction passage.

It is, of course, time consuming and cumbersome to remove the guide wire and its effectiveness is lost when removed. Accordingly, it would be beneficial to be able to move the guide wire as little as possible, or not at all following tissue penetration. I have also determined that a different needle structure would be more useful with other types of scopes, i.e., endoscopes, or other long tubular structure used within a patient's body, usually a hollow organ, such as the windpipe, lungs, the esophagus, the stomach or intestines. The present design be used in the lungs to obtain lymph node mediastinum which is located outside the windpipe to allow diagnosis of the various diseases as well as to keep track of the staging of lung cancer. It can also be used in the esophagus, stomach and intestine for diagnosis purposes or even therapy, the latter including drainage of cystic lesions like pancreatic cysts thereby eliminating the necessity of a more serious operation and is the only means of which I am aware of for suitably draining pancreatic cysts. The device can also be used in the GI track, not withstanding that the size of the space is larger and that the unique psysiological quality of the GI track, in particular peristalsis activity would tend to lead a needle away from the biopsy target when such were located outside of the GI track lumen.

Reference is made to the Jamshedi soft-tissue biopsy needle/syringe in which two of four ribs or fins along the plunger are provided with regularly spaced apart saw-tooth indentations that will cooperate with a pair of opposed locking and stop flanges to allow the physician to position the plunger at a predetermined amount of suction as determined by the axial position of the plunger within the syringe. The flanges are provided in a plate fixed to the proximal end of the syringe barrel and the plunger is positioned by twisting the plunger when a pair of the saw-tooth indentations align with the flanges. The plurality of indentations renders the plunger difficult to move axially and is fixed to the syringe.

SUMMARY OF THE PRESENT INVENTION

In the first embodiment of the present invention the tissue collecting needle is itself moveable between extended and retracted positions relative to a smooth hub or tip located at the distal end of a hollow, flexible catheter. The smooth hub needle is usually withdrawn leaving only the distal end exposed. This tip end is designed so that it will not damage either the internal channel of the endoscope nor the patient and it reduces any trauma or possible injury to the patient should the tip inadvertently touch the mucosa of the hollow organ into which the endoscope has been inserted.

Reciprocally mounted within that hollow catheter is a stylet or guide wire and a hollow needle is mounted at the distal end of that guide wire. The needle includes a base structure adjacent the connection to the guide wire that is provided with a lateral opening into the hollow portion of the needle. The needle is sufficiently long so that the opening while reciprocal relative to the hub member it will never move into that hub member but will rather remain within the confines of the catheter. A rubber 0-ring or similar sealing mechanism is provided so as to surround the needle between the opening and the hub to provide a seal between the interior of the hollow catheter and the exterior of the hollow needle during reciprocation and also while the needle is in its retracted and extended positions. The guide wire is reciprocal through a fixed distance that will allow he tip of the hollow needle to extend outwardly beyond the hub when in its extended position and a retracted point where the needle tip lies internally within the hub. In both conditions, a passageway or fluid-tissue channel is created between the interior wall of the hollow flexible catheter and the outer surface of the flexible guide wire, through the lateral opening in the needle into and through the hollow needle thereof.

It should be noted that no removal of the guide wire is necessary to develop the suction passageway. Rather, the suction passageway is continuously defined between the exterior of the guide wire and the interior of the outer flexible catheter. The distal end of the guide wire is sealed into its conventional leurlock assembly, so when the latter is closed and suction is applied, no leakage will occur around the guide wire connection point within the leur lock structure. Rather, the suction source will only be connected via the passageway between the catheter and the guide wire through the lateral opening at the base of the needle to the tip of the needle. Thus, while even a partial removal of the guide wire is eliminated, the resulting structure provides sufficient rigidity for the whole instrument and most importantly directly to the needle so that the needle can be withdrawn and advanced repeatedly into the lesion, often a very important factor in obtaining an adequate tis sue sample from various portions or the lesion of the area in which the biopsy tissue is desirably withdrawn. This was not possible in prior types of needles because once the reinforcement provided by the guide wire was withdrawn, in order to provide a vacuum or negative pressure passageway the plastic catheter would often bend or kink when axial compressive force was applied to the proximal end of the assembly. This was especially true when prior devices were used in the GI track because the spaces there are so much bigger that tending and kinking would more readily occur.

Further, by employing this needle design, the internal cavity formed between the exterior of the guide wire and the interior of the outer catheter is sufficiently large so that even thick pus or cystic fluids can be evacuated through this apparatus.

A second embodiment of the present invention relates to a three piece device in which the same outer hollow, flexible catheter is used together with an inner hollow, flexible catheter as well as a guide wire provided to move axially within the inner most catheter and the latter being itself reciprocal relative to the outer catheter. In this embodiment, the hollow needle is secured or appropriately affixed at the distal end of the inner catheter rather than to the guide wire. The outer catheter will have the same or virtually the same construction as in the first embodiment previously discussed. Similarly, the hollow needle is provided with a lateral aperture, adjacent the needle/catheter connection, and is, together with the inner catheter, similarly reciprocal relative to the distal end of the outer catheter such that the aperture will also remain positioned interiorally of the hub area at the distal end of the outer catheter in either its fully extended or retracted positions.

The inner most catheter has a length that is slightly longer than the length of the outer catheter so that when the controlling portion of the leur lock is locked in place the inner catheter will be placed under a slight degree of compression thereby assuring some amount of axial force being directly applied against the needle. The third element, the guide wire, is sized so as to tightly yet slidably fit within the inner catheter and will have a length such that when the needle is fully projected in its forward or advanced position and the inner catheter is compressed, the sharp-beveled tip of the guide wire will extend a predetermined distance beyond the distal end of the hollow catheter. With the guide wire protruding from the tip of the hollow needle there will be no possibility of the needle becoming plugged by unwanted tissue as the needle is inserted through normal tissue toward the site where the biopsy tissue is desirably to be obtained. When the hollow needle reaches the biopsy site, the guide wire will then be withdrawn a short or predetermined distance so that its distal end will lie proximate to but axially behind the side opening provided in the hollow needle thereby opening that opening into the hollow needle. At that point, suction will be applied to the cavity defined between the interior of the outer catheter and the exterior of the inner catheter which will lead directly to the tip of the hollow needle through the lateral opening in the needle and allow negative pressure to be applied directly to the tissue being sampled. Because the guide wire is designed to fit tightly within the inner catheter the guide wire will provide a seal therein so that negative pressure or suction will only be applied via the chamber between the two catheters and through the hollow needle. Sufficient diagnostic tissue or material can be obtained and it will be easier to interpret the results from the tissue being sampled because there will be a lack of contamination by otherwise unwanted tissue or cells and it will be possible as well to obtain a relatively large quantity of the diagnostic material or tissue since the continued presence of the guide wire continues to provide rigidity to the catheter assembly. It should be understood that the guide wire need only be withdrawn a short distance, and only as far as a point proximate the side hole in the needle to permit the negative pressure or suction force to flow from the chamber between the inner and outer catheters into the hollow needle. The fact that the length of the inner tubing is made slightly longer than that of the length of the outer tubing will both allow the beveled-tipped guide wire to protrude from the needle when both the inner catheter is locked in place and secondly the compressed inner tubing will function as a sort of spring to place axial force directly on the needle so that it will not retract into the metal hub when resistance is met during penetration into and through tissue.

Further, the fact that the guide wire itself is maneuverable within the inner most catheter, the distal end of the apparatus can be rendered more flexible and thus more maneuverable thereby able to negotiate sharper turns in order to be appropriately directed at the desired target area. As the guide wire is withdrawn further from the area adjacent the needle, the distal end of the device becomes that much more flexible.

Additionally, it should be pointed out that with the second embodiment the inner catheter and its ability to operate between its advanced and retracted positions is limited by a stop mechanism provided at the proximal end so that the inner catheter cannot be overdrawn assuring that the tip of the needle will remain within or closely adjacent the hub end of the outer catheter and will not be overdrawn past the rubber O-ring type seal so as to assure the positive transmission of negative pressure to the needle.

In a third embodiment, which is somewhat similar to the one just described, the guide wire has been shortened and the base of the needle structure, at a point adjacent but proximate of the lateral opening, will be compressed, dented or otherwise formed so that when the guide wire is inserted and its leur lock properly closed the tip of the guide wire will engage the compressed area or dent thereby providing excellent rigidity for the needle. Because the guide wire is located on the proximate side of the opening into the needle, withdrawal of the guide wire is not necessary at all in order to establish a path for negative pressure to the needle with the needle apparatus remaining rigid throughout the period when suction is applied. In those instances where greater flexibility is required, such as when maneuvering the tip of the outer catheter, the guide wire can be retracted either a fixed distance or as much as is desired to provide a great deal of flexibility in the flexibility of the distal end of the apparatus.

The present invention also relates to an improved syringe plunger locking structure to permit the physician to appropriately and with precision lock the plunger in a position that will apply a predetermined amount of negative pressure or suction, even in low light situations where these procedures are often carried out.

These and other objects, features, and characteristics of the present invention, as well as the methods and operation and functions of the related elements of the structure comprising the present invention, and to the combination of parts and the economies of their manufacture, will all become more apparent upon consideration of the following description and the appended claims with reference to the accompanying drawings, all of which form a part of this specification, wherein like reference numerals designate corresponding parts in the various figures.

BRIEF DESCRIPTION OF THE DRAWINGS

FIG. 1A is a diagrammatic cross-sectional view of the distal end of a first embodiment of a transendoscopic needle with the needle in its retracted position;

FIG. 1B shows the proximal end of the transendoscopic needle shown in FIG. 1;

FIG. 2a is a cross-sectional view similar to FIG. 1 showing the needle in its extended position;

FIG. 3c is a cross-sectional view taken along line 3C-3C in FIG. 3b;

FIG. 3d is a cross-sectional view showing the connection for the inner catheter;

FIG. 4a and 4b, respectively, are cross-sectional views of the distal and proximal ends of the needle shown in FIGS. 3a and 3b wherein both needle and the guide wire are in their advanced or extended positions;

FIGS. 5a and 5b, respectively, are cross-sectional views of the distal and proximal ends of the needle shown in FIGS. 3a and 3b with the needle in its extended position and the guide wire partially retracted;

FIG. 6a is a cross-sectional view of the distal end of another embodiment of the present invention;

FIG. 6b is a cross-sectional view of the distal end of another embodiment of the present invention;

FIG. 7 is a side elevational view of a syringe for use with the present invention;

FIG. 8 is a bottom plan view of a plunger lock for attachment to a syringe;

FIG. 9 is a cross-sectional view of the syringe taken along line 9–9 in FIG. 7;

FIG. 10 is a cross-sectional view similar to that shown in FIG. 9 but with the plunger in its turned and locked position; and FIG. 11 is a diagrammatic view of the proximal end of a syringe body in which the plunger lock is integrally formed thereon.

Figure 3B:
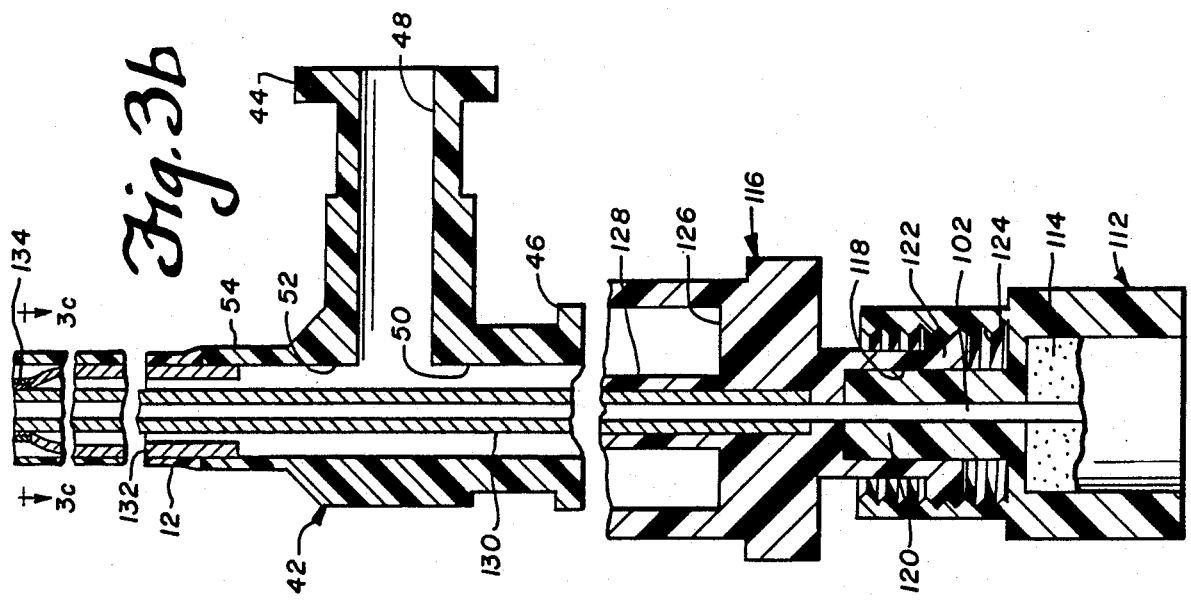
FIGS. 3a and 3b, respectively, show the distal and proximal ends of a second embodiment of the present invention wherein the needle and guide wire are shown in their retracted positions.

DETAILED DESCRIPTION OF THE PREFERRED EXEMPLARY EMBODIMENTS OF THE PRESENT INVENTION

The present invention includes three embodiments which will be discussed in sequence below.

Turning first to FIGS. 1a–2 b wherein the in both its retracted and extended positions.

With reference first to FIG. 1a, the transendoscopic needle assembly, generally indicated at 10, is comprised of an outer flexible hollow catheter 12 to which a hardened tip 14 is fixed, the tip having a rounded or smoothed end face 16. The catheter is preferably formed as an extruded tube from polyethylene although other plastic materials could be used. While I prefer to form tip 15 preferably formed from metal, such as stainless steel, the tip could also be formed from a variety of materials including other metals such as aluminum, polycarbonate, thermoplastic or thermoset resins or other formable plastic materials.

The connection between tip 14 and the distal end of catheter 12 can either be accomplished by way of screw threads, as indicated at 18, or by way of seaing ribs, by use of an adhesive or by some combination of these approaches. What is essential is that tip 14 be secured to and retained in place on the distal end of catheter 12 so that it cannot fall off or be left in the patient's body. With the tip in place the end of the catheter is protected, the catheter assembly will be easily threaded through an endoscope or bronchoscope and the interior surface thereof will not be damaged and the patient will be protected from trauma that might otherwise occur without the presence of the smooth, rounded surface 16.

Reciprocally mounted within the hollow catheter is a guide wire 20 and, as shown in FIG. 1a, a hollow needle 22 is welded, soldered or otherwise secured, as for example by the solder shown at 24, to the distal end of guide wire 20. This connection will preferably close the proximal end of hollow needle 22 and guide wire 20 can be directly joined to needle 22 or by a mounting block 26 can be interposed there between. Hollow needle 22 is also provided with a lateral opening 28 formed or cut into the side wall of needle 22 adjacent the proximal end where needle 22 is joined to guide wire 20. Opening 28 serves as art of the fluid communication passageway within the device which passageway also includes the hollow interior of catheter 12 about guide wire 20 as will be explained in detail below.

The distal end of this assembly 10 also includes a seal 30 provided between the outer surface of hollow needle 22 and the interior surface of the hollow flexible catheter 12. As shown, this seal is provided in the form of a rubber or elastomeric O-ring that will move or roll as the needle and catheter moved relative to one another.

It should also be understood that the interior of the metal tip 14 will cooperate with the gauge of needle 22 so that a relatively close but slidable fit will exist therebetween.

Turning our attention to FIG. 1b, a conventional leur lock is generally indicated at 40 which consists of a primary housing 42 made of plastic or nylon and having a standard syringe coupling 44 provided on one side and a second similar coupling area also provided at 46. The interior of housing 42 is hollow and is comprised of two main passageways 48 and 50 which meet at right angles to one another, with a third passageway 52 extending axially away from passage 50 but with a reduced diameter as shown.

Housing 42 also includes a cylindrical extension 54 surrounding and defining passageway 52, and a tubular joining member 56 is threadily within the interior of extension 54. Alternatively, the metal member 56 can be glued or secured perhaps by force fit arrangement within the interior of the hollow extension 54. Member 56 is preferably metal but other material could be used provided they produced a tubular member which exhibits sufficient lateral and axial strength to connect the outer catheter and housing 42 together.

Catheter 12 is slid over the hollow connecting member 56 and can be adhered there about either by friction fit or by an adhesive. Adhesive can also be used at the joint between the proximal end of catheter 12 and the distal end surface of extension 54.

Figure 2B:
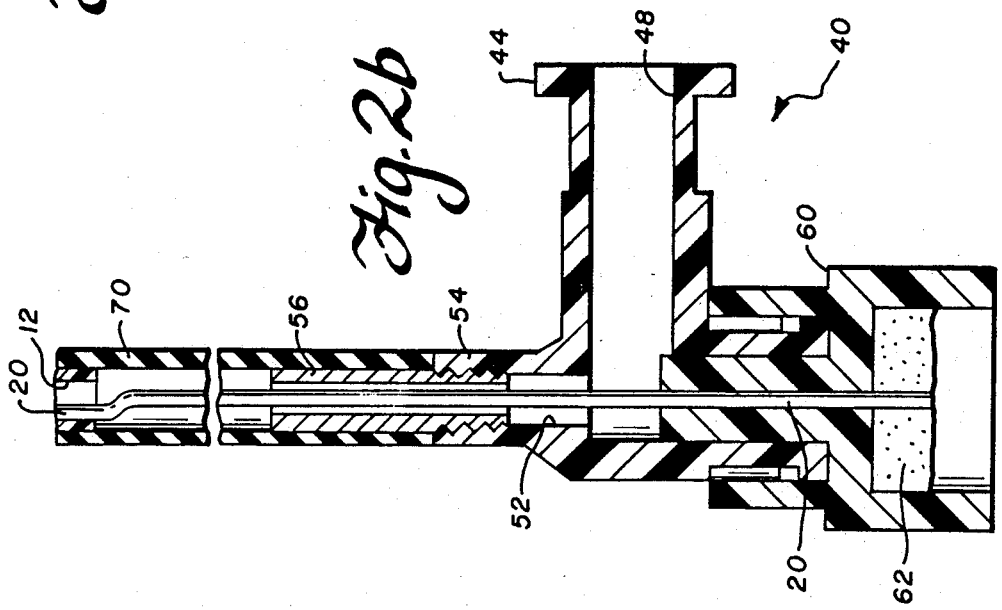
FIG. 2b is a cross-sectional view similar to FIG. 1B as showing the proximal end in its closed position.

Guide wire 20 also extends through the hollow connecting member 56, through passageways 52 and 50 and is secured within a leur cap 60 by means of an epoxy adhesive 62. The interior of cap 60 is provided with a bayonet or screw-type mounting arrangement that will cooperate with coupling 46 and also includes an axially extending plug member 64 that will fit into passageway 50 when cap 60 is locked in place on housing 42, as indicated in FIG. 2b, thereby sealing passageway 50. Thus, when a syringe is attached to coupling 44 and suction or vacuum applied to passageway 48 that suction will, in turn, be applied to the interior of hollow needle 22 via passageway 52, the hollow interior of member 56 through hollow catheter 12 and then through opening 28 as the distal end of the catheter adjacent needle 22 is sealed by the sealing device 30.

With reference still to FIG. 1b, it should be noted that guide wire 20 is bent or kinked, as indicated at 66, so that the distal end of the hollow tubular member 56 will act as a stop member and prevent further retraction of guide wire 20. This limits the amount of axial movement of guide wire 20 and, accordingly, controls the position of the tip of needle 22 relative to the distal end of catheter 12 and in particular relative to tip 14. It is preferred to limit travel of needle 22 so that the tip will not be retracted beyond the interior of tip 14 whereby the distal tip of needle 22 will not be retracted to a position beyond sealing means 30 as to do so would destroy that seal. All that is necessary is that the distal end of needle 22 be retractable interiorily of end 16.

In the advanced position of needle 22, as shown in FIGS. 2a and 2b, the tip will be extended well past the outer surface 16 but the lateral opening 28 will still lie within catheter 12 and preferably axially spaced from the proximal side or the interior end of tip 14 as well as on the proximal side of sealing means 30. Needle 22 has an overall length of about 25 mm and opening 28 is positioned about 20 mm from the distal end. When advanced, the needle would extend about 10-12 mm beyond surface 16.

In terms of joining catheter 12 to the leur lock assembly 40, either the catheter itself can be connected as explained above, or alternatively, as shown in FIG. 2b, a separate exterior mating sheath 70, formed from plastic material, can be mounted about and sealed to the tubular hollow extension member 56 and catheter 12 in turn adhered by any conventional means to the interior of sleeve 70. In addition, sleeve 70 could also be used as an additional part of the joint in FIG. 1b by being mounted over extension 54 and catheter 12, as indicated in phantom at 72, to provide a stronger joint between the catheter and leur lock 40.

Turning now to the next embodiment, as shown in FIGS. 3a-5b, the outer hollow catheter and its distal and proximal ends are formed as described above with respect to the first embodiment.

However, the hollow needle, now indicated at 100, has been slightly modified as it is not connected to guide wire 102 but rather directly to an inner catheter 104 which will have an outer diameter less than the inner diameter of the outer catheter 12. Needle 100 is joined to the distal end of the inner catheter 104 by any convenient means such as by forming the needle with a reduced collar portion, as indicated at 106, over which the distal end of the interior catheter 104 can be secured either by friction fit or preferably by the use of a suitable adhesive therebetween. Needle 100 can also be provided with an enlarged shank portion 108 adjacent the proximal end of needle 100 with a portion of this enlarged area being cut away to define a lateral opening 110 into the interior of the hollow needle. In other respects, the sliding fit of needle 100 within tip 14 and its operation with respect to the sealing device 30 will be the same as discussed above with respect to the first embodiment.

As previously was the case, guide wire 102 will be secured within a cap portion 112 by means of an epoxy or other adhesive sealant 114 so that the reciprocation and movement of guide wire 102 will be under the control of cap 112 and no fluid leakage will be possible through the joint therebetween.

The leur lock as shown in FIG. 3b includes three portions housing 42, end cap 112 and an intermediate member 116. On one side, of intermediate member a standard leur lock recess 118 is provided to receive the depending portion 120 from cap 112 as well as a coupling arrangement, generally indicated at 122 that will inter-fit with the mating coupling portion 124 of cap 112. Since these couplings are standard design, further description thereof is not deemed to be warranted for a full and complete description of this portion of the apparatus.

The opposite side of the intermediate member 116 includes a coupling portion 126 designed to cooperate with coupling 46 on housing 42. In addition, intermediate member 116 includes a central tubular hub portion 128 in which the proximal end of a tubular mounting sleeve 130 is secured, as for example by use of n adhesive or friction fit. Mounting sleeve 130 is preferably metal, for example stainless steel, although other materials, such as hard or thermoplastic resins could be used. Sleeve 130 is about 100 mm in length and has an internal diameter of 1.3 mm and an outer diameter of *1.5* mm.

As shown in FIG. 3b, guide wire 102 extends into and through tubular mounting sleeve 130 and will reciprocate axially therein.

With continuing reference to 3b, catheter 12 is secured at its proximal end to another tubular sleeve 132, that can be formed similarly to sleeve 130. Sleeve 132 is adhered to the interior of extension 54 on housing 42, again either by use of threads, by means of a force fit, friction connection, by means of an adhesive, or by some combination of these Tubular sleeve 132 has a length of approximately 25 mm with a portion of that length inner fitting interiorally within extension 54, the remainder providing a force fit or adhesive connection between itself and catheter 12. As shown in FIGS. 3b-3d, the distal end of tubular member 132 is squeezed together so that its opposite sides lie proximate the exterior surface of the tubular mounting sleeve 130. In addition, mounting sleeve 130 is provided with a fixed stop member 134 positioned about 25-30 mm from the distal end thereof which will have an outer diameter such that prior to squeezing the distal end of tubular member 132 stop member 134 will slide therethrough, but which after the deformation will be engaged the squeezed distal end of tubular member 132 and be positively stopped thus controlling the relative and axial movement between needle 100 and catheter 12.

This is also shown in FIGS. 3c and 3d wherein the tubular mounting sleeve 132 is shown as being bent inwardly so as to engage stop member 134 provided on tubular mounting sleeve 130 within which the guide wire 102 operates and on which inner catheter 104 is secured.

As shown in FIG. 3c, tubular mounting sleeve 130 extends for some length beyond stop 134, about 25-30 mm, and this length provides for either a friction fit or an adhesive seal between its outer surface and the inner flexible catheter 104. It should be kept in mind that the interior diameter of tubular sleeve 130 is approximately the same as that of the interior dimension of inner catheter 104 with both being approximately the same as the outer diameter of guide wire 102 so that a sliding but relatively secure fit is provided therebetween. This will assure that when suction is ultimately applied to the needle assembly, as was discussed above with the first embodiment, leakage will not occur backward along the area between the interior of catheter 104 and the guide wire 102. With respect to other exemplary dimensions, for the outer catheter it has an inner diameter of about 1.8 mm and an outer diameter of about 2.0, the inner catheter has an outer diameter of about 1.5 mm and an inner diameter of about 1.3, mm the guide wire has an outer diameter of about 1.3 mm and the needle is preferably a 22 to 19½ gauge needle.

Figure 3A:
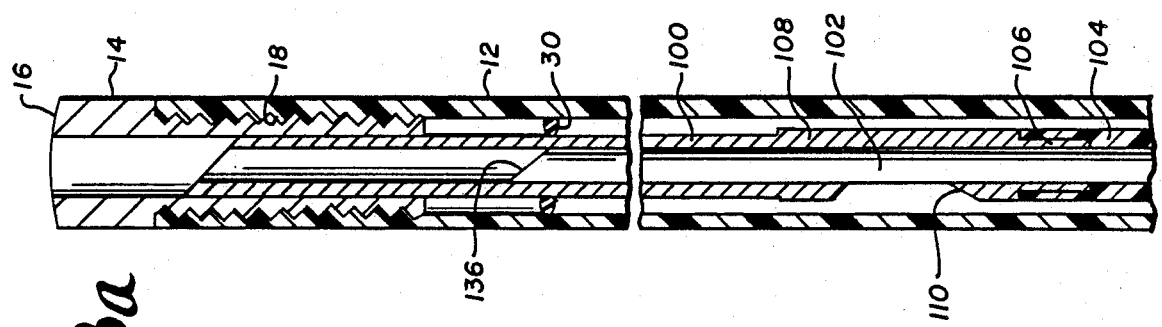

As shown in FIGS. 3a and 3b, while the intermediate leur lock member 116 is not in its engaged position, but rather spaced axially from housing 42, cap 112 is fixed in place to the intermediate member 116. Thus, at this point the relationship between guide wire 102 and needle 100 is fixed, one relative to the other. As shown in FIG. 3a, the beveled end 136 of guide wire 102 is spaced from the distal end of needle 100 in contrast to the relative position between needle 100 and guide wire 102 shown in FIG. 4a where the distal end of guide wire 102 projects beyond the end of needle 104. This is accomplished by making the length of inner catheter 104 sightly longer, preferably from about 5 to about 10 millimeters longer, than the overall length of the outer catheter, including tip 14, so that when intermediate member 116 is fixed in place on housing 42, inner catheter 104 will be compressed axially. This places a desired amount of axial pressure on needle 100 and at the same time allows additional relative axial movement between the needle and the inner catheter on the one hand and guide wire 102 on the other thereby causing the beveled dipped end wire 136 to project beyond the distal end of needle 100. The fully closed condition of housing 42 intermediate member 116 and cap 112 is shown in FIG. 4b.

In the position shown in FIG. 4a and 4b, while it is possible to penetrate tissue because the sharp beveled-tipped end 136 of guide wire 102 extends beyond needle 100, the presence of the guide wire within the needle simultaneously prevents penetrate tissue and simultaneously prevent the needle 100 from being filled or plugged by unwanted tissue. Thus, until needle 100 is placed at the biopsy site, guide wire 102 will provide both a way of penetrating tissue and preventing collection of undesirable tissue.

Having arrived at the biopsy site, it is then possible to loosen cap 112 and axially slide guide wire 102 a slight distance rearwardly so that the forward beveled end thereof lies close to or adjacent but on the proximal side of opening 110. This will open a fluid pathway via passageways 48 and 52, through the passageway formed between the interior surface of tubular mounting sleeve 132 and the exterior of tubular mounting sleeve 130, through the non-squeezed side portions of the tubular mounting sleeve 132, as shown in FIG. 3c, and then through the space between the inner and outer catheters, through opening 110 and into hollow needle 100. This is the position shown in FIGS. 5a and 5b.

Turning now to the next embodiment as shown in FIG. 6a, the structure of the outer catheter is again the same as that discussed above with respect to the first embodiment. Similarly, the structure of the needle is also similar to that of the second embodiment wherein the hollow needle 200 is connected to an inner catheter 202. However, rather than having a structure that allows the guide wire 204 to extend through the needle, the needle itself, which also includes an opening 206 cut in the side wall of an enlarged hollow portion 208, includes a detent or crimped portion 210 formed either by deforming the outer sidewall or by modifying the hollow interior of portion 208 that will sufficiently restrict the internal diameter of the hollow interior of the needle so that the guide wire 204 will not be able to extend beyond that crimped portion. However, because crimped portion 210 lies proximally of opening 206, even with the wire 204 in engagement with crimped portion 210 the passageway formed between the outer catheter and the inner catheter 202 will be directly connected with the interior of needle 200 through opening 206 without any necessity for moving or removing the guide wire 204. Thus, if it is desired to retain the stiffness for purposes of collecting the tissue sample, and for sequentially penetrating the biopsy site, that stiffness can be provided by having guide wire 204 remain positioned in contact with crimped portion 210 as shown in FIG. 6a. Alternatively, if it is desired to have the distal end of the apparatus be more flexible, guide wire 204 can be retracted to a point interiorly of catheter 202 leaving only the inner and outer catheters as the support for the distal end of the apparatus thereby making that distal portion much more flexible and maneuverable.

FIG. 6b shows another embodiment of the distal end structure. The distal end of the outer catheter 12 and tip 14 remain the same as in the previously described embodiments. However, the hollow needle structure has been modified. Hollow needle 250 has a circular cutting edge 252 at its distal end formed, for example, by cutting and then conically sharpening the end as shown. The distal end portion is also provided with a lateral opening 254 from the interior through the side 256. The opening is shaped so that a first angled cut surface 258 extends from the side wall inwardly at an angle of about 30° and intersects a second angled cut surface 260 which is at about a 45° angle from horizontal. The lower side wall edge 262 is formed into a cutting edge so that tissue samples can be collected by or through opening 254 as well as through the distal end via cutting edge 252. In addition, the guide wire 204 is provided with an angled distal end 264 thereby defining a sharp penetrating point 266 for allowing insertion through tissue.

It should also be understood that the opening 254 could also be incorporated into the hollow needles of the other embodiments, for example in needles 22, 100 and 200, so that those could include this additional tissue gathering structure.

Also, the shaped tips of the needles could also vary to accommodate the particular sites of where tissue is to be sampled. For example, if it was desired to obtain samples by scraping procedures rather than by penetration through tissue, another shaped needle distal end could be employed.

Turning now to FIGS. 7-11, the present invention also relates to a modified syringe for use with mounting assembly 44 for providing a predetermined amount of suction within the biopsy needle structure.

Attention is also directed to my earlier U.S. Pat. No. 4,532,935 and in particular to FIG. 1, 13 and 15 of that patent.

The present invention, as in FIG. 7 relates to a syringe that will fit onto a conventional coupling of leur lock housing and includes a syringe body 300 and a plunger 302 provided with a seal member 304 on the plunger's distal end. When the front portion of the syringe body 300 is attached to coupling 44 and the plunger is withdrawn a vacuum will be created within the catheter system sufficient to pull biopsy tissue into the needle.

As was explained in my above-referenced patent, the plunger fins have been modified so as to include grooves cut into two oppositely positioned fins in order to be able to position the plunger at a specific withdrawn point. The plunger is formed with four intersecting fins, webs or ribs, each positioned at 90° from adjacent fins, webs with these fins being indicated by numerals 306, 308, 310 and 312, respectively. With reference to FIG. 7, two grooves are shown as being formed by cutouts provided in ribs 306 and 310, the grooves being indicated at 314 and 316.

The opening into the syringe body in my above-identified patent included two inwardly extending locking flanges that were formed as extensions of the planar surface surrounding the distal end of the body portion. Together they provided a surface for supporting the portion of the fins exposed by the groove. However, the problem with this prior structure was that after pulling the plunger out a prescribed distance a physician could overturn the plunger moving the grooved fins past the flanges so that rather than having those fins aligned directly over and supported by the locking flanges, the plunger would simply be pulled back into the syringe body.

With reference to FIGS. 8-10, the present invention relates to a separate integrally formed attachment member, generally indicated at 320, which fits over the planar wall of a conventional of syringe shown in FIG. 7 at 322. Such a planar end would not include any locking flanges but rather simply an opening through which the plunger can be inserted or removed.

Member 320 is comprised of a planar top surface 324 and a planar bottom surface 326 which are joined together by a short vertical front wall 323 so that the planar surfaces 324 and 326 are separated at least by the distance of the planar end wall 322 at the proximal end of the syringe body.

The bottom planar surface 326 is formed with a U-shaped opening 328 having a diameter or opening width that is the same as or slightly greater than the outer diameter of the syringe body so that it can fit therearound. The top planar surface 324 is provided with a shaped cutout that opens outwardly away from front wall 323, with the cutout area including two inwardly extending locking flanges 330 and 332 as well as an inwardly directed stop member 334 which is defined between two recesses respectively indicated at 336 and 338, positioned between the stop member and the locking flanges. The locking flanges 330 and 332 each include a flattened interior edge, one of which is indicated at 340, with the opening from the exterior of the attachment into this cutout area being provided by two angled surfaces 342 and 344. Recesses 336 and 338 are positioned at about 90° one from the other and are approximately aligned with the angle surfaces 344 and 342, respectively, with those two surfaces and recesses approximately defining an X-shaped pattern. As shown in FIG. 9, the plunger, and in particular fins 306-312 are shown in the position where ribs 310 and 308 are approximately aligned with surfaces 342 and 344, respectively, while fins 306 and 312 respectively lie within recesses 338 and 336. In this position, plunger 302 can be moved axially back and forth within the syringe body 300 without any impediment as a relatively large space is provided in which to receive the plunger and in particular fins 306-312. Once the plunger is pulled out a predetermined distance, such as the distance defined by grooves indicated at 314, 316 or similar grooves provided elsewhere as desired, along the plunger 302, the plunger can be twisted 45° as shown in FIG. 10. At this point, fin 312 will engage stop member 334, as shown in FIG. 10, and prohibit further rotation of plunger 302. Fins 306 and 310 will also in a directly overlie locking flanges 330 and 332 and will prevent plunger 302 from moving axially back into syringe body 300. Stop 334 will provide a positive stop and prevent the possibility of overturning the plunger thereby providing more positive control over the positioning of the plunger relative to locking flanges 330 and 332.

This attachment member 320 can be formed from a variety of materials, preferably injection molded from plastic but it could be formed from metal or other formable materials. Further, the attachment can be provided in various sizes to coordinate with conventional syringe sizes.

With reference to FIG. 11, it should also be understood that the end wall structure of the syringe body 300' could be formed as an integral unit with the locking flanges 330' and 332' as well as the stop member 334' being formed in one piece.

While the invention has been described in connection with what is presently considered to be the most practical and preferred embodiments, it is to be understood that the invention is not to be limited to the disclosed embodiments, but on the contrary, is intended to cover various modifications and equivalent arrangements included within the spirit and scope of the appended claims.

What is claimed is:

1. A removable attachment for use with a syringe, said syringe including an elongated barrel having a planar end wall at one end thereof and a separate plunger slidably received in said barrel, said plunger being formed from opposing webs having a cruciform cross section, at least one pair of notches being formed in opposing webs, said planar end wall being oriented at approximately 90? to a barrel axis, said attachment comprising two spaced apart end wall members joined together by at least one side wall member, each of said end walls including means defining an opening for receiving portions of said syringe therein, one of said end walls including first and second flanges extending into said opening means on said one end wall at substantially diametrically opposed locations, and a third member extending into said opening means on said one end wall and positioned at a location intermediate to said first and second flanges, the opening means in the other end wall opening to an edge of said other end wall so that said attachment can be slidably mounted on said planar end wall and about the barrel to properly position the plunger relative to the barrel and to look the plunger in at least one desired position.

2. An attachment as in claim 1 wherein said opening means in each end wall comprises a slot means extending inwardly from an exterior edge.

* * * * *